US011806061B2

(12) United States Patent
Bauer

(10) Patent No.: US 11,806,061 B2
(45) Date of Patent: Nov. 7, 2023

(54) AND METHOD FOR PROXIMAL AND DISTAL SCREW FIXATION IN INTRAMEDULLARY TIBIAL NAILS

(71) Applicant: Jordan Andre Bauer, Woodbury, CT (US)

(72) Inventor: Jordan Andre Bauer, Woodbury, CT (US)

(*) Notice: Subject to any disclaimer, the term of this patent is extended or adjusted under 35 U.S.C. 154(b) by 57 days.

(21) Appl. No.: 17/980,832

(22) Filed: Nov. 4, 2022

(65) Prior Publication Data
US 2023/0145104 A1   May 11, 2023

Related U.S. Application Data

(60) Provisional application No. 63/276,083, filed on Nov. 5, 2021.

(51) Int. Cl.
| | |
|---|---|
| *A61B 17/90* | (2006.01) |
| *A61B 17/88* | (2006.01) |
| *A61B 17/17* | (2006.01) |
| *A61B 17/00* | (2006.01) |

(52) U.S. Cl.
CPC .......... *A61B 17/90* (2021.08); *A61B 17/8872* (2013.01); *A61B 17/1725* (2013.01); *A61B 2017/00991* (2013.01)

(58) Field of Classification Search
CPC ..... A61B 17/90; A61B 17/8872; A61B 17/17; A61B 17/1717; A61B 17/1725; A61B 17/62; A61B 17/72; A61B 17/921; A61B 17/92
See application file for complete search history.

(56) References Cited

U.S. PATENT DOCUMENTS

| | | |
|---|---|---|
| 2,719,688 A | 10/1955 | Seifert |
| 3,492,054 A | 1/1970 | Boggs et al. |
| 3,674,294 A | 7/1972 | Kirkham |

(Continued)

OTHER PUBLICATIONS

Testrite Instrument Co., Inc.; Snap Lock Telescopic Tube Lock (G); https://www.testriteoem.com/products/telescoping-aluminum-tubing-lock; retrieved from the Internet Aug. 15, 2022; whole document.

(Continued)

*Primary Examiner* — Tracy L Kamikawa
(74) *Attorney, Agent, or Firm* — Ware, Fressola, Maguire & Barber LLP

(57) ABSTRACT

An IM tibial nail aiming guide for providing proximal and distal screw fixation in an intramedullary nailing (IMN) of a tibia includes an attachment that connects and disconnects easily from a jig's proximal handle. Specifically, the IM tibial nail aiming guide functions as an aiming guide for accurate fixation of all the respective proximal and distal screw holes in a tibial nail. The IM tibial nail aiming guide has a length and angle that are adjustable, affording the ability to use this IM tibial nail aiming guide with any tibial nail. This IM tibial nail aiming guide is made of radiolucent material that allows for a confirmatory fluoroscopic imaging to verify that both the proximal and distal screws are fixated appropriately. The IM tibial nail aiming guide permits a more accurate, safe, versatile, and efficient approach to tibial IMN.

20 Claims, 5 Drawing Sheets

(56) References Cited

U.S. PATENT DOCUMENTS

| | | | |
|---|---|---|---|
| 4,450,834 A * | 5/1984 | Fischer | A61B 17/645 606/56 |
| 4,803,976 A | 2/1989 | Frigg et al. | |
| 4,865,025 A | 9/1989 | Buzzi et al. | |
| 5,474,561 A * | 12/1995 | Yao | A61B 17/1725 606/98 |
| 5,492,243 A | 2/1996 | Brandhorst | |
| 5,540,691 A | 7/1996 | Elstrom et al. | |
| 5,971,984 A * | 10/1999 | Taylor | A61B 17/62 606/56 |
| 6,027,506 A | 2/2000 | Faccioli et al. | |
| 6,039,742 A | 3/2000 | Krettek et al. | |
| 6,093,192 A * | 7/2000 | Abel | A61B 17/1725 606/98 |
| 6,129,729 A | 10/2000 | Snyder | |
| 6,514,253 B1 * | 2/2003 | Yao | A61B 17/1725 128/892 |
| 6,635,061 B1 | 10/2003 | Snyder | |
| 6,656,189 B1 | 12/2003 | Wilson et al. | |
| 6,663,631 B2 | 12/2003 | Kuntz | |
| 6,695,266 B1 | 2/2004 | Tsai | |
| 8,231,629 B2 | 7/2012 | Lerner et al. | |
| 9,249,565 B2 | 2/2016 | Merrifield | |
| 9,800,980 B2 | 10/2017 | Palmer et al. | |
| 9,820,760 B2 * | 11/2017 | Purohit | A61B 17/72 |
| 10,288,196 B2 | 5/2019 | Hu | |
| 10,390,859 B2 * | 8/2019 | Sakkers | A61B 17/6441 |
| 10,820,916 B2 | 11/2020 | Fernandez et al. | |
| 11,123,116 B2 | 9/2021 | Ehmke et al. | |
| 2004/0215204 A1 | 10/2004 | Davison et al. | |
| 2013/0085502 A1 | 4/2013 | Harrold | |
| 2015/0305791 A1 | 10/2015 | Purohit | |
| 2021/0015500 A1 | 1/2021 | Nassonov | |
| 2021/0113219 A1 * | 4/2021 | Rettew | A61B 17/164 |

OTHER PUBLICATIONS

Sugatsune; "HG-RCT12-C Ratchet Hinge"; https://www.sugatsune.com/product/ratchet-hinge; retrieved from the Internet Aug. 15, 2022; whole document.

Sugatsune; "HG-MA95A-R Multi Angle Locking Hinge"; https://www.sugatsune.com/product/multi-angle-locking-hinge; retrieved from the Internet Aug. 15, 2022; whole document.

Pinet-Industrie; "Multi Angle Locking Hinge A with Lever"; https://www.pinet-industrie.com/en/products/35524-multi-angle-locking-hinge-a-with-lever; retrieved from the Internet Aug. 15, 2022; whole document.

Levin, P. E., Schoen, R. W., Jr, & Browner, B. D. (1987); "Radiation exposure to the surgeon during closed interlocking intramedullary nailing"; The Journal of bone and joint surgery. American vol. 69(5), 761-766.

Moreschini, O., Petrucci, V., & Cannata, R. (2014); "Insertion of distal locking screws of tibial intramedullary nails: A comparison between the free-hand technique and the SURESHOT® Distal Targeting System"; Injury, 45(2), 405-407. See https://doi:10.1016/j.injury.2013.09.023.

Allard, A., Letissier, H., Le Nen, D., Dubrana, F., & Di Francia, R. (2021); "Evaluation of the accuracy of the Sureshot® electromagnetic targeting system in distal locking of long-nailed humeral diaphyseal fractures"; Orthopaedics & traumatology, surgery & research : OTSR, 107(2), 102785. See https://doi.org/10.1016/j.otsr.2020.10278.

Veen, E. J., Ettema, H. B., Zuurmond, R. G., & Mostert, A. K. (2011); "Are there any advantages in using a distal aiming device for tibial nailing? Comparing the Centro Nailing System with the Unreamed Tibia Nail"; Injury, 42(10), 1049-1052. See https://doi.org/10.1016/j.injury.2011.03.056.

Gugala Z, Nana A, Lindsey RW; "Tibial intramedullary nail distal interlocking screw placement: comparison of the free-hand versus distally-based targeting device techniques"; Injury2001;32(Suppl. 4 SD):21-5.

Variloc; Variloc Steel Hinges, Heavy Duty Steel 360, 220, and 180 hinges; "Heavy Duty Allow Steel Locking Hinges"; hittps://www.adjustablelockingtech.com/products_variloc_steel.php; retrieved from internet on Jul. 15, 2022; whole Document.

Testrite Instrument Co., Inc.; Square Telescoping Tubing Locks; https://www.testriteoem.com/products/square-telescoping-tubing-locks; retrieved from Internet Jul. 15, 2022; whole document.

Testrite Instrument Co., Inc.; "Tube Ends, Joiners & Attachments"; https://www.testriteoem.com/products/tube-ends-joiners-attachments; retrieved from Internet Jul. 15, 2022; whole document.

* cited by examiner

AND METHOD FOR PROXIMAL AND DISTAL SCREW FIXATION IN INTRAMEDULLARY TIBIAL NAILS

CROSS-REFERENCE TO RELATED APPLICATIONS

This application claims benefit to provisional application Ser. No. 63/276,083, filed 5 Nov. 2021, which is hereby incorporated by reference in its entirety.

BACKGROUND OF THE INVENTION

1. Field of the Invention

The invention relates to a method and apparatus for performing orthopedic surgery; and more particularly relates to a surgical instrument in the form of an IM tibial nail aiming guide for performing intramedullary nailing (IMN) on a fractured tibia of a patient.

2. Description of Related Arts

Intramedullary nailing (IMN) of a tibia is a mainstay treatment of diaphyseal tibial fractures. Once the medulla of the patient's tibia is reamed and a proper nail length and diameter is determined, proximal and distal screws must be placed for proper fixation. In known tibial IMN systems reviewed by the inventor, there is a proximal aiming guide that assists in the proximal screw placement. The known proximal aiming guide is a C-shaped apparatus that attaches to the tibial nail's insertion handle of a jig. Once attached, the variety of openings in the proximal aiming guide can be used to accurately drill and fix anterior-posterior (AP), transverse, and oblique screws through the proximal nail. An AP and lateral x-ray are then taken using a C-arm fluoroscope to confirm proper placement of the proximal screws. Subsequently, distal screw placement is performed. However, the majority of known tibial IMN systems require the free-hand method of distal screw fixation. Distal locking of the IMN tibial nail can be cumbersome and time consuming when performed using the free-hand method.

Surprisingly, most of the known tibial IMN systems do not have distal aiming guides for distal screw placement, thus the free-hand method is necessary. The free-hand method requires excessive radiation exposure. Most tibial IMN procedures exposes the patient and medical professionals to roughly 7.0-8.0 millirem/surgery (Roentgen equivalent man). See reference no. [1] below. For example, a surgeon who performs on average five IMN of the tibia per week experiences 1,820 millirem/yr, which is equivalent to 182 chest x-rays according to the Department of Health and Environmental Control. Thus, designing a method and apparatus to diminish the amount of radiation required will protect the areas of the body not covered or minimally covered by a lead vest worn in the operating room. For example, one known system, such as Smith&Nephew's Trigen SUREshot®, has lowered radiation exposure and intraoperative time. However, the Trigen SUREshot® cannot be used in patients with pacemakers and has a learning curve requiring a certification before use. See reference no. [2] below. Additionally, the accuracy of the Trident SUREshot® has been variable and inconsistent, with some studies finding lower success rates compared to the free-hand method when performing tibial, femoral, and long humeral IMN. See reference no. [3] below.

Furthermore, some orthopedic device companies, such as Medtronic, Orthofix, DePuy Synthese Products Inc., and Sryker Trauma GmbH each have complete tibial nailing systems that extend down to the nail's distal screw sites. However, these systems are limited in their use. Independent studies using Orthofix's device called Centronail found that it lengthened operative time and was technically cumbersome to use. Moreover, the Centronail Titanium Tibial Nail system had a difficult learning curve and the unfamiliarity with the system led to material failures. See reference no. [4] below. This Centronail Titanium Tibial Nail system requires multiple attachments and adaptors to assemble for distal screw locking. A survey given to surgeons testing the Centronail Titanium Tibial Nail system concluded that they stopped using the system when the locking procedure was not successful and resorted to their trusted technique of free-hand locking to save time on behalf of their patients. See reference no. [4] below. Additionally, radiation exposure with the Centronail Titanium Tibial Nail system was variable. Fluoroscopy time was either the same or shorter than the free-hand method. See reference nos. [4,5] below. Lastly, the Centronail Titanium Tibial Nail system was not designed for screw dynamization, potentially leading to a delayed union of the fracture site. See reference no. [4] below. Ultimately, the Centronail Titanium Tibial Nail system does not improve operative time, has variable amounts of radiation exposure, is challenging to use, and lacks the option of dynamization. It was concluded that the Centronail Titanium Tibial Nail system did not add any benefit to the tibial IMN procedure. See reference no. [4] below. Ultimately, the current distal targeting devices offered on the market are not optimized compared to the free-hand method and lacks the benefits offered by the present invention.

The inventor reviewed the database of the US Patent and Trademark Office and found other devices that were designed to locate distal screw sites of intramedullary nails. These designs respectively used x-ray guidance, all-mechanical devices, and optic-mechanical devices (e.g., see U.S. Patent and application Ser. Nos. 12/308,877; 16/128, 173; 16/514,014; 4,803,976; 6,129,729; 6,635,061; 6,656, 189; 4,865,025; 6,027,506; 6,039,742; 5,540,691). All of these devices claim to identify some of the distal screw holes in IM nails, but not all of them. None of these devices provides simultaneous identification of all proximal and distal screw holes and the ability of distal screw dynamization.

SUMMARY OF INVENTION

The present invention provides a new apparatus and method for screw fixation in tibial IMN. The apparatus may take the form of an IM tibial nail aiming guide that consists of a proximal and distal C-shaped aiming guide connected by a support bar mechanism (e.g., two or more support bars) with couplers (e.g., four or more couplers) to lock the proximal and distal aiming guides that are adjustable in length and angle respectively. The support bars and couplers have locking devices, that when activated yield a completely rigid structure. Each support bar has two couplers, one at each end where it meets the proximal and distal aiming guides. The ability to adjust the entire length of the IM tibial nail aiming guide and the angle of the proximal and distal aiming guides affords the ability to use the IM tibial nail aiming guide with any existing producer's IM nails.

The IM tibial nail aiming guide according to the present invention is different from all other known devices and systems described above, because it is an extension that easily attaches and detaches from the proximal aiming handle of the tibial IM nail. Once attached, the guide holes are instantly aligned with the tibial nail's proximal and distal screw sites. These guide holes provide accurate guidance of proximal and distal screw fixation. Since this IM tibial nail aiming guide is an attachment, it will allow surgeons to maintain the use of their preferred products with the added benefit of an easily attachable and removable component that will decrease operative time, radiation exposure, afford the option of screw dynamization, and maintain distal screw accuracy compared to the known free-hand method.

The IM tibial nail aiming guide according to the present invention is more beneficial than the known devices and systems described above, because the IM tibial nail aiming guide is system independent and not user dependent. The learning curve is very low since surgeons will have continued use of their preferred system, and the apparatus is one complete rigid structure once locked. There is no need to adjust any measurements or make any alterations once the IM tibial nail aiming guide is positioned in the jig. And the use of the aligned proximal and distal aiming guides makes proper screw placements quicker, more accurate, and decreases radiation exposure compared to the free-hand method. Additionally, the IM tibial nail aiming guide allows for versatility in its use. Each unique nail length and angle is accommodated by the design of this IM tibial nail aiming guide, and it can be used on either the right or left leg interchangeably. Furthermore, the option to easily detach this IM tibial nail aiming guide allows the surgeon to proceed with the free-hand method of distal screw placement, if necessary.

Specific Embodiments

According to some embodiment, the present invention may take the form of an intramedullary (IM) tibial nail aiming guide, e.g., for coupling to an IM tibial nail having proximal and distal holes for receiving proximal and distal screws and also having an IM tibial nail proximal insertion handle, featuring a proximal aiming guide, proximal hinge joints, a distal aiming guide, distal hinge joints and telescopic support bars.

The proximal aiming guide may include, or be configured with, proximal guide holes passing through for accurate drilling and receiving proximal screws for fixing to proximal holes in an IM tibial nail, and an IM tibial nail coupling portion configured to couple to the IM tibial nail proximal insertion handle when the IM tibial nail aiming guide is connected to the IM tibial nail.

The proximal hinge joints may be configured to couple to the proximal aiming guide and angle and lock the proximal aiming guide in relation to the IM tibial nail to be inserted into the medulla of the patient's tibia.

The distal aiming guide may include, or be configured with, distal guide holes for accurate drilling and receiving distal screws for fixing to distal holes in the IM tibial nail.

The distal hinge joints may be configured to couple to distal aiming guide and angle and lock the distal aiming guide in relation to the IM tibial nail to be inserted into the medulla of the patient's tibia.

The telescopic support bars may be configured to couple the proximal hinge joints and the distal hinge joints and to expand or contract and lock adaptively in order to change the length between the proximal aiming guide and the distal aiming guide to accommodate different tibial nails having different tibial nail lengths.

The intramedullary (IM) tibial nail aiming guide may include one or more of the following features:

The proximal aiming guide may take the form of a C-shape with an AP proximal guide hole, two transverse proximal guide holes, two oblique proximal guide holes each with static and dynamic options.

The distal aiming guide may take the form of a C-shape with two AP distal guide holes, two transverse distal guide holes, two oblique distal guide holes each with static and dynamic options.

Each proximal hinge joint may include an angle modulator, an angle locking device, and an angled measuring dial guide.

Each distal hinge joint may include an angle modulator, an angle locking device, and an angled measuring dial guide.

Each telescopic support bar may include at least one telescopic extender configured to change the length of each telescopic support bar and also includes a locking mechanism configured to rigidly fix the telescopic support bars at a desired length.

The intramedullary (IM) tibial nail aiming guide may be made in whole or in part of a radiolucent material.

The proximal hinge joints may include two or three proximal hinge joints; the distal hinge joints may include two or three distal hinge joints; and the telescopic support bars may include two or three telescopic support bars, each telescopic support bar configured to couple a respective proximal hinge joint to a respective distal hinge joint.

The IM tibial nail coupling portion may include location pins to be inserted through location pin holes on the proximal insertion handle when the IM tibial nail aiming guide is connected to the IM tibial nail.

The intramedullary (IM) tibial nail aiming guide may include a locking mechanism or thumb screw configured to securely tighten the IM tibial nail aiming guide to the proximal insertion handle creating a complete rigid structure.

The intramedullary (IM) tibial nail aiming guide may include two or three hinge and support bar combinations, where each hinge and support bar combination includes a respective proximal hinge joint, a respective distal hinge joint and a respective telescopic support bar formed or configured as a respective one piece construction for coupling to and connecting together the proximal aiming guide and the distal aiming guide.

The Method

According to some embodiment, the present invention may take the form of a method for coupling an intramedullary (IM) tibial nail aiming guide to an IM tibial nail having proximal and distal holes for receiving proximal and distal screws and also having an IM tibial nail proximal insertion handle, e.g., featuring steps of:

configuring a proximal aiming guide with proximal guide holes passing through for accurate drilling and receiving proximal screws for fixing to proximal holes in an IM tibial nail, and with an IM tibial nail coupling portion configured to couple to the IM tibial nail proximal insertion handle when the IM tibial nail aiming guide is connected to the IM tibial nail;

coupling proximal hinge joints to the proximal aiming guide to angle and lock the proximal aiming guide in relation to the IM tibial nail inserted into the medulla of the patient's tibia;

configuring a distal aiming guide with distal guide holes for accurate drilling and receiving distal screws for fixing to distal holes in the IM tibial nail;

coupling distal hinge joints to the distal aiming guide to angle and lock the distal aiming guide in relation to the IM tibial nail to be inserted into the medulla of the patient's tibia; and coupling telescopic support bars to the proximal hinge joints and the distal hinge joints to expand or contract and lock adaptively in order to change the length between the proximal aiming guide and the distal aiming guide to accommodate different tibial nails having different tibial nail lengths.

The method may include, or be implemented with, one or more of the features set forth herein.

BRIEF DESCRIPTION OF DRAWING

The drawing includes FIGS. 1-5, as follows:

FIG. 4A is a lateral view and FIG. 4B is an oblique view.

DETAILED DESCRIPTION OF VARIOUS EMBODIMENTS

Figure 1:
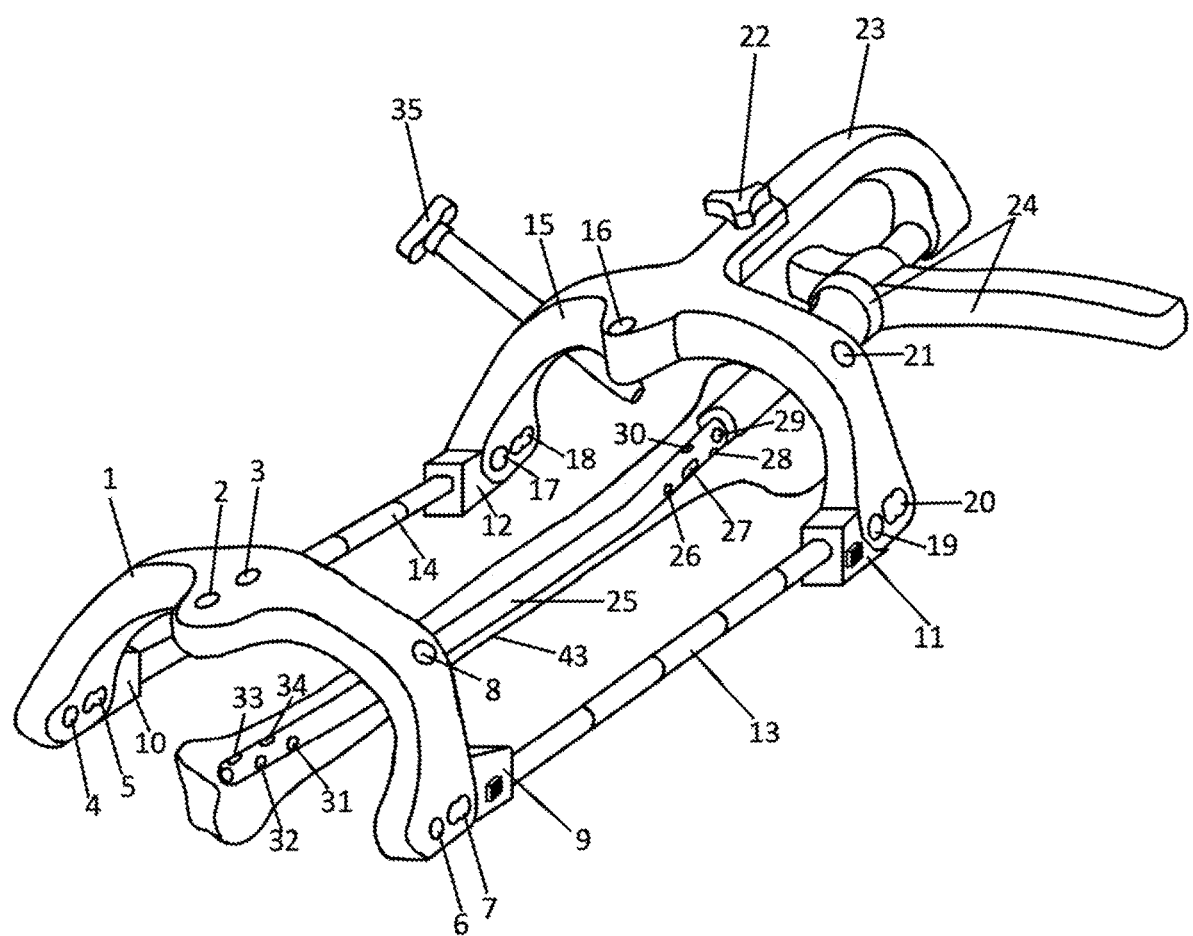
FIG. 1 is a perspective view of the IM tibial nail aiming guide according to some embodiments of the present invention, e.g., attached to a proximal handle with a tibial nail fixed to a retention bolt.

FIG. 1 shows a new and unique IM tibial nail aiming guide according to the present invention, e.g., that includes an aiming guide combination having a distal aiming guide (1) connected by support bars (13, 14) to a proximal aiming guide (15). The IM tibial nail aiming guide couples to a tibial IM nail combination having a tibial IM nail (25), a proximal insertion handle (23) and a suprapatellar or infrapatellar nail cannula (24).

In particular, the distal aiming guide (1) locates and provides guidance of drilling through all the distal screw or guide holes (2-8). The distal aiming guide (1) has various guides that include anterior-posterior (AP) guides (2-3), transverse guides (4-7) with dynamic and static options, and oblique distal guides (8). Note, there is another distal oblique guide not shown in FIG. 1 that is on the adjacent side of the distal aiming guide (1) opposite to the oblique distal guide (8). The distal aiming guide (1) also has distal aiming guide angle modulators with locking mechanisms (9-10). See and compare the proximal aiming guide angle modulators with locking mechanisms (11-12) of the proximal aiming guide (15). Two support bars (13-14) consist of two side bars. These support bars (13-14) have telescopic abilities with associated locking mechanisms as shown and described in relation to FIG. 3A below.

The proximal aiming guide (15) is designed to locate and provide guidance of drilling through all the proximal screw or guide holes (16-21). The proximal aiming guide (15) has various guides that include an AP guide (16), transverse guides (17-20) with dynamic and static options, and oblique proximal guide (21). Note, there is another proximal oblique guide not shown in FIG. 1 that is on the adjacent side of the proximal aiming guide (15) opposite to the oblique proximal screw guide (21). The trajectory of the other proximal oblique guide is visualized by a trocar (35) shown partially inserted through the other proximal oblique guide in FIG. 1. In operation, the trocar (35) with a soft tissue sleeve (not shown) and the appropriate drill sleeve (not shown) are used to visually mark on the skin where drilling will commence. A stab incision is made where the soft tissue sleeve touches the skin surface. Dissection is carried out to the point where the soft tissue sleeve can be advanced to reach cortical bone. The appropriate drill and drill sleeve are used to drill through both cortices. Subsequently, measurements are taken, and the appropriate screw length and type is chosen and fixed securely using the soft tissue sleeve through the trocar (35). This method described maintains the traditional method currently used for proximal screw fixation in tibial IMN. All other guided drilling and screw fixation is performed as previously described for all the other proximal and distal screw sites.

Figure 2:
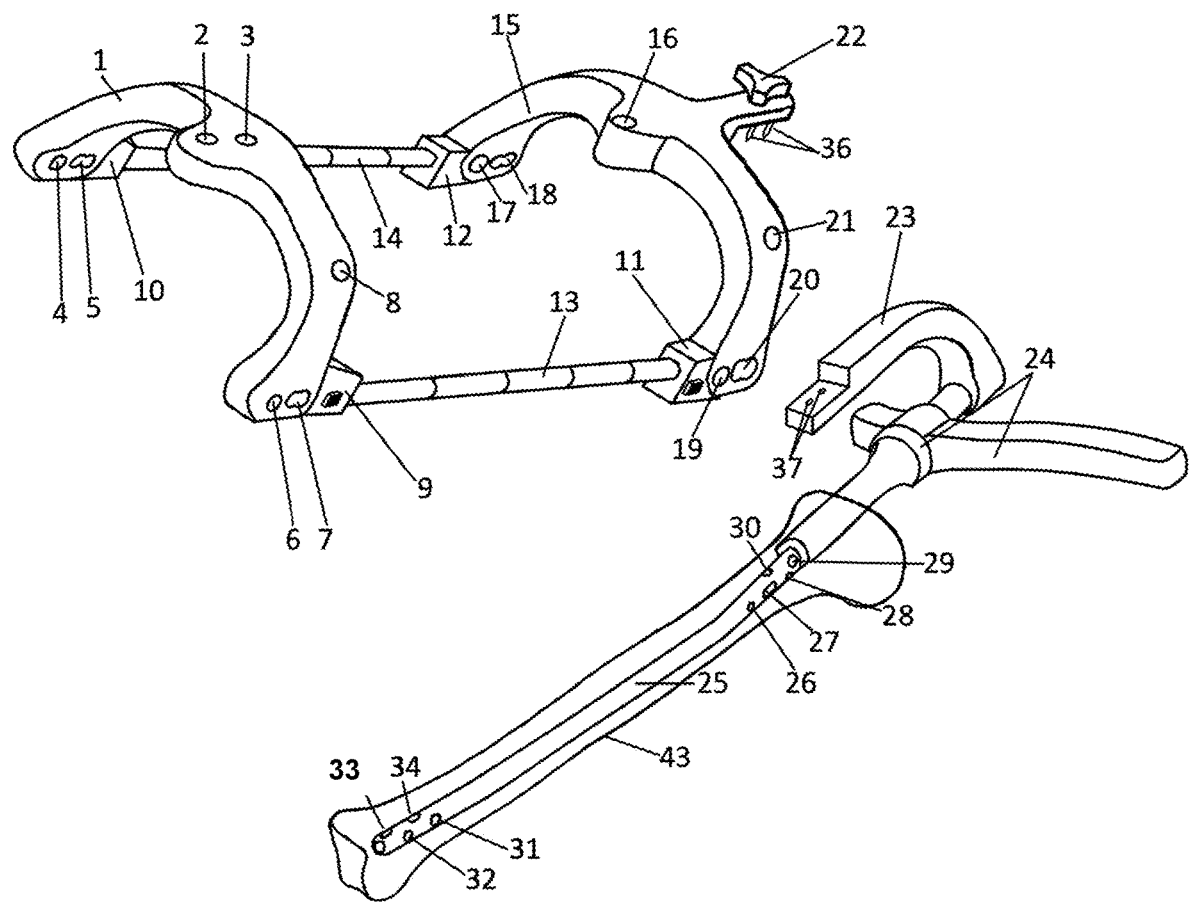
FIG. 2 is an exploded view of the IM tibial nail aiming guide shown in FIG. 1, e.g., detached from the proximal handle of the tibial IM nail.

The locking mechanism or thumb screw (22) is used to securely fix the IM tibial nail aiming guide to the tibial nail proximal insertion handle (23) of the jig. The suprapatellar or infrapatellar nail cannula (24) and the associated drill sleeve and trocar are used during the tibial IMN for guided K-wire insertion and guided medullary canal entry reaming. Once the tibial medulla is reamed, a retention bolt (not shown) is slid through the tubular part of the proximal insertion handle (23) and fastened to the tibial IM nail (25) using a retention bolt driver (not shown). Once the construction of the proximal insertion handle (23), retention bolt, and tibial IM nail (25) is complete, the tibial IM nail (25) is driven down entering through the suprapatellar or infrapatellar nail cannula (24) first and subsequently through the patient's tibial medullary canal of the patient's tibia (43). The tibial IM nail (25) has a proximal and distal bend and various proximal and distal screw holes (26-34). The angles of the nails shape and the number of screw holes varies between company and system. FIG. 1 shows the tibial IM nail (25) with transverse proximal screw holes (26-27), oblique proximal screw holes (28-29), and AP proximal screw hole (30). Additionally, there are transverse distal screw holes (31-32), and AP distal screw holes (33-34). FIGS. 1 and 2 do not show an oblique distal screw hole in the tibial IM nail (25), which does exist in some company's products. See and compare the oblique proximal screw holes (28-29) of the proximal aiming guide (15) in relation to the oblique proximal guide (21). (It is noted for the sake of completeness, and set forth by way of example, that FIGS. 1-2 also do not show transverse and oblique proximal screw holes on the other side of the tibial IM nail (25) associated with the transverse guides (17-18) and the other oblique distal guide opposite to the oblique proximal screw guide (21) that correspond to the transverse proximal screw holes (26-27) and the oblique proximal screw holes (28-29) as shown; and also do not show distal screw holes on the other side of the tibial IM nail (25) associated with the transverse guides (4-5) that correspond to the distal screw holes (31-32) as shown.

FIG. 2 shows the IM tibial nail aiming guide detached from the proximal insertion handle (23). FIG. 2 visually represents how the IM tibial nail aiming guide is easily attached and detached from the proximal insertion handle (23) with the tibial IM nail (25) construct.

In operation, the IM tibial nail aiming guide is attached to the tibial IM nail (25); the angles of the proximal and distal aiming guides (1, 15) are set and locked rigidly with respect to the tibial IM nail's proximal and distal bend prior to attachment to the proximal insertion handle (23); and similarly, the lengths of the two side bars (13-14) are adjusted to be aligned with the nail length being used prior to attachment to the proximal insertion handle (23). Once the appropriate angles and length of the IM tibial nail aiming guide are established so that the proximal and distal guides of the proximal and distal aiming guides are aligned with the proximal and distal holes of the IM tibial nail for receiving proximal and distal screws, the tibial IM nail (25) is detached from the IM tibial nail aiming guide and inserted into the medulla of the patient's tibia (43); and then the IM tibial nail aiming guide is easily re-attached to the proximal insertion handle (23) of the tibial IM nail (25), e.g., by inserting location pins (36) on the proximal aiming guide (15) through location pin holes (37) on the proximal insertion handle (23). The locking mechanism or thumb screw (22) is used to securely tighten the IM tibial nail aiming guide to the proximal insertion handle (23) creating one complete rigid structure for attaching to the patient's tibia (43).

The Telescopic Support Bar

Figures 3, 3A:
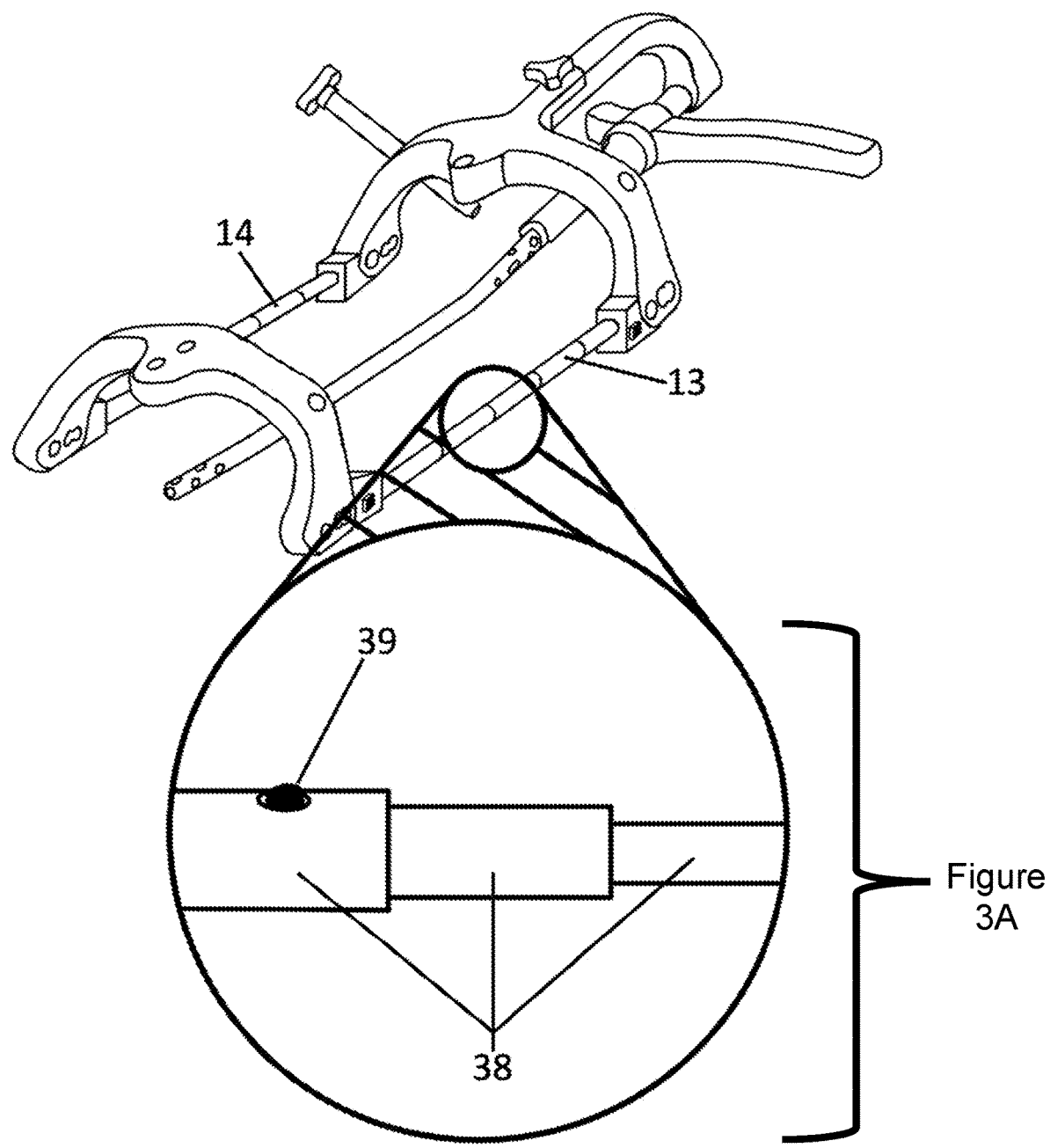
FIG. 3 is another perspective view of the IM tibial nail aiming guide shown in FIG. 1.
FIG. 3A is an enlarged view of one of the side support bars demonstrating telescoping ability and a locking mechanism of the IM tibial nail aiming guide shown in FIG. 3.

FIG. 3A is an enlarged view of one of the side support bars (13). By way of example, each support bar (13-14) may include one or more telescopic extenders (38) that provide the ability to change the length of each support bar (13-14) to accommodate any tibial IM nail length on the market. Each support bar (13-14) also has an easy locking mechanism (39) that rigidly fixes the support bars (13-14) at the desired length. Each telescopic extender (38) may include a measuring scale (not shown) configured to allow one to measure and determine with accuracy the length of a telescopic extension of one extender (38) in relation to another extender (38). By way of example, the support bars (13, 14) may be connected to the hinge joints (9, 10, 11, 12) via welding, e.g., including where the support bars (13, 14) and the hinge joints (9, 10, 11, 12) are made of the same or substantially similar material and suitably welded together. By way of further example, and consistent with what one skilled in the art would appreciate, the support bar (13) and the hinge joints (9, 11) may be made of or from the same material and formed as one piece, then suitably connected to the distal and proximal aiming guides (1, 15); and similarly, the support bar (14) and the hinge joints (10, 12) may also be made of or from the same material and also be formed as one piece, then suitably connected to the distal and proximal aiming guides (1, 15).

Techniques for providing tubes having telescopic and locking ability like elements (38-39) are known in the art, and the scope of the invention is not intended to be limited to any particular type or kind thereof either now known or later developed in the future. By way of example, see other techniques disclosed in U.S. Pat. Nos. 2,719,688; 3,674,294; 5,492,243; 6,695,266; and 10,288,196, which are all hereby incorporated by reference. The telescope tube and locking techniques disclosed in the aforementioned patents can be used, or easily adapted to be used, e.g., by one skilled in the art. By way of further example, a product known as a snap lock telescope tube lock may be used that is sold by Testrite Instruments Co., Inc., doing business at 216 S. Newman St., Hackensack, N.J. 07601.

By way of still further examples, the IM tibial nail aiming guide may include a support bar mechanism having a telescoping bar with a clutch lock and knurl with a manual or pneumatic release.

a split collar tube lock with a manual or pneumatic release;

an internal cam lock with a manual or pneumatic release;

a spring button lock with tubes at predetermined positions with a manual or pneumatic release;

a spring button clutch lock with a manual or pneumatic release;

a snap lock with a manual release; a telescoping bar with a snap lock with a pneumatic release;

a set knob tube lock with a manual or pneumatic release;

a mini economy tube lock with a manual or pneumatic release;

a swaging with a manual or pneumatic release;

a non-locking tube; a telescoping bar with a shock cord tubing;

manually locking swivel mechanisms and swivel joints;

pneumatically locking swivel mechanisms and swivel joints;

embedded washer(s); or a shaft collar and set screw.

The Hinge Joint and Locking Mechanism

Figures 4, 4A, 4B:
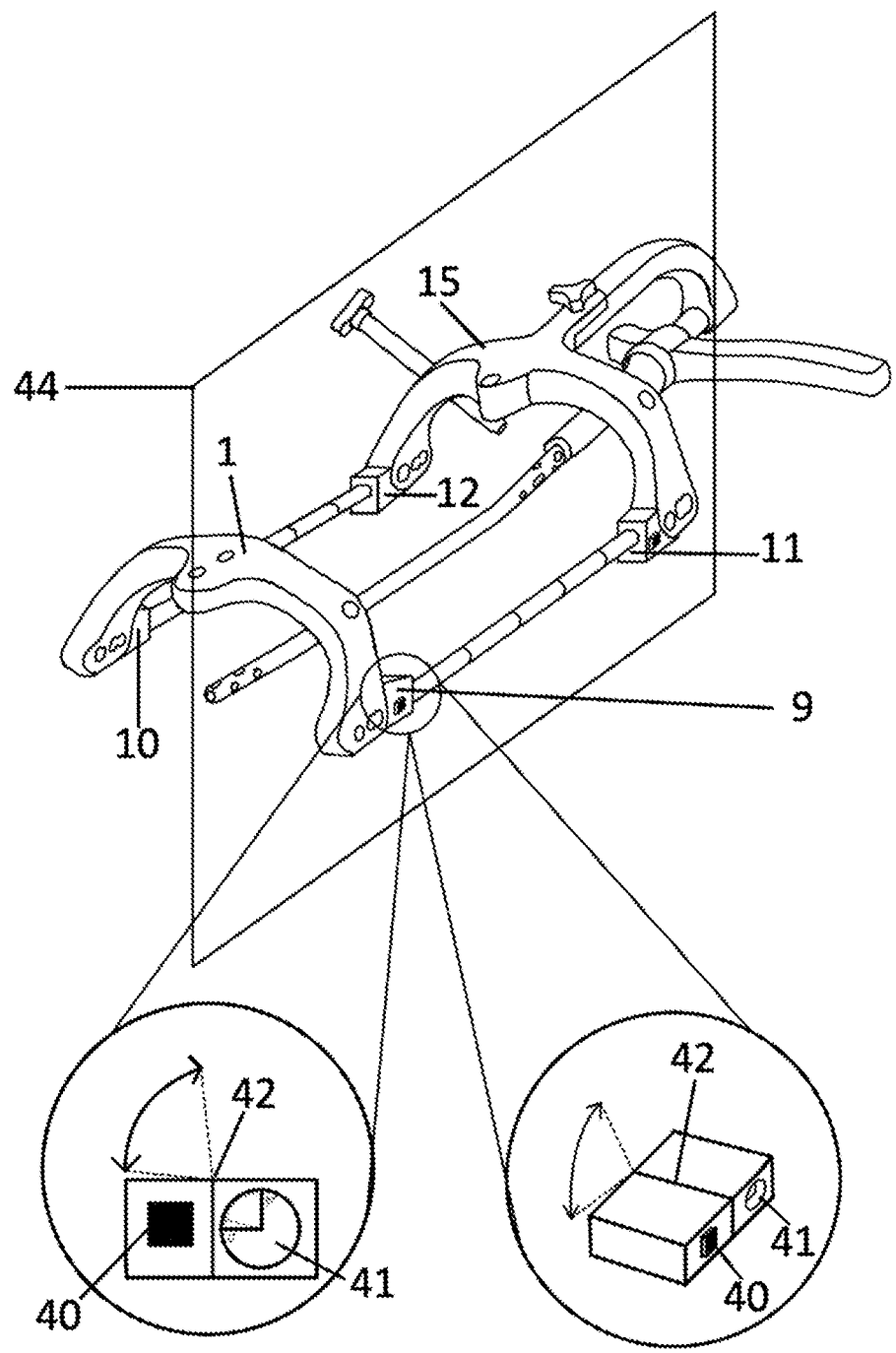
FIG. 4 is another perspective view of the apparatus shown in FIG. 1.
FIGS. 4A and 4B shows two enlarged views one of the hinge joints demonstrating augmentation of the angle and locking mechanism of the IM tibial nail aiming guide shown in FIG. 4; where

FIGS. 4A and 4B shows two enlarged views of one of the locking mechanisms (9) that may be formed as hinge joints. This hinge joint has an angle modulator (42), an angle locking device (40), and an angled measuring dial guide (41). This allows for accurate angling and rigid fixation of the proximal and distal aiming guides (1,15) independent to each other to accommodate any tibial IM nail's proximal and distal bends.

Techniques for hinging and locking one element to another like elements (40-42) are known in the art, and the scope of the invention is not intended to be limited to any particular type or kind thereof either now known or later developed in the future. By way of example, the hinge joints (9, 10, 11, 12) may be connected to the distal and proximal aiming guides (1, 15) via injection molded interlocks, e.g., consistent with how the hinge joints angle and lock are connected in that disclosed in U.S. Pat. No. 11,123,116. By way of further example, and consistent with what one skilled in the art would appreciate, the injection molded interlocks may include, or take the form of, tapered, side and angled interlocks.

By way of further example, see other techniques disclosed in U.S. Pat. Nos. 3,492,054; 6,663,631; 9,800,980; and 9,249,565, which are all hereby incorporated by reference. The hinging and locking techniques disclosed in the aforementioned patents can be used, or easily adapted to be used, e.g., by one skilled in the art. By way of further example, see products known as HG-RCT12-C ratchet hinge and HG-MA95A-R multi angle locking hinge sold by a company named Sagatune; a product known as multi angle locking hinge A with lever sold by PINET Industrie, 9 rue de l'etang, PIA Paris Nord 2, BP 62036.

By way of still further examples, the IM tibial nail aiming guide may include a hinge joint mechanism having
- a multi angle toggling leaver locking hinge with a manual release or a pneumatic release;
- a multi angle toggling ratchet locking hinge with a manual release or a pneumatic release;
- a multi angle toggling push button activated locking hinge with a manual release or a pneumatic release;
- a multi angle toggling wheel locking hinge with a manual release or a pneumatic release; or
- an angle measuring dialed guide.

Summary of Other Features of the Present Invention

Embodiments are also envisioned in which the IM tibial nail aiming guide according to the present invention may include, or take the form of, one or more of the following:

An IM tibial nail aiming guide that may include the following:
- a proximal and distal aiming guide with two or more rigid bars, that are adjustable in length to accommodate any nail length;
- these bars each have telescoping abilities to change in length, a measuring scale along their length for accuracy, and a locking mechanism that fixes the IM tibial nail aiming guide at the desired length;
- at proximal and distal ends of the bars where they meet the proximal and distal aiming guides, there are hinge joints;
- there are two or more hinge joints proximally and two or more distally, with two hinge joints at each end of each bar;
- these hinge joints allow for adjustment of the angle of the proximal and distal aiming guides independently with respect to the sagittal plane; and
- once the desired angle is achieved, the hinge joints can be locked, rigidly fixing the proximal and distal aiming guides at the desired angles.

The IM tibial nail aiming guide may function as an aiming guide that provides accurate drilling and fixation of anterior-posterior, transverse, and oblique proximal and distal screws in tibial intramedullary nails; and may be easily connected and disconnected to the jigs proximal handle.

A method according to the present invention may be implemented for accurately and simultaneously locating proximal and distal tibial intramedullary nail holes while inside the medulla of a patient's fractured tibia, e.g., and include steps as follows:
- Once the appropriate tibial intramedullary nail length and diameter are confirmed for the patient's tibial medulla, adjusting the IM tibial nail aiming guide's length to be aligned with the respective nail length and distal screw holes;
- locking the bars to fix the IM tibial nail aiming guide at the desired length;
- adjusting the angle of the proximal and distal aiming guides to correspond to the degree of proximal and distal nail bend respective to the IM tibial nail being used;
- locking the couplers to fix the guides at the desired angles, so as to rigidly lock and align the IM tibial nail aiming guide to the proper length and angle of the nail's screw holes;
- attaching the IM tibial nail aiming guide to the proximal insertion handle;
- once complete, confirming accurate alignment of the guide holes relative to the IM tibial nail holes;
- subsequently, detaching the IM tibial nail aiming guide from the proximal insertion handle, and advancing and impacting the IM tibial nail through the patient's tibial medulla;
- using a C-arm fluoroscope to confirm appropriate nail depth and then re-attaching the IM tibial nail aiming guide to the proximal insertion handle;
- next, placing a trocar and soft tissue sleeve through the proximal guide holes, drilling through both cortices of each hole used, and fixing the AP, transverse, and oblique screws using traditional methods;
- using a C-arm fluoroscope to confirm proper placement of the proximal screws; attention is then drawn to the distal screw holes; and
- using the IM tibial nail aiming guide's distal aiming guide in the same manner as described for proximal screw fixation and appropriate fixation is confirmed using the fluoroscope.

The advantages of the method may also include the following:
- decrease operative time and infection risk due to the quick identification of both proximal and distal screw sites;
- decrease intraoperative radiation exposure due to less use of the fluoroscope compared to other current methods;
- maintain the traditional method of proximal screw fixation;
- increase accuracy of distal screw fixation compared to other current methods; and/or
- afford the option of dynamization of proximal and distal screws.

FIG. 5

Figure 5:
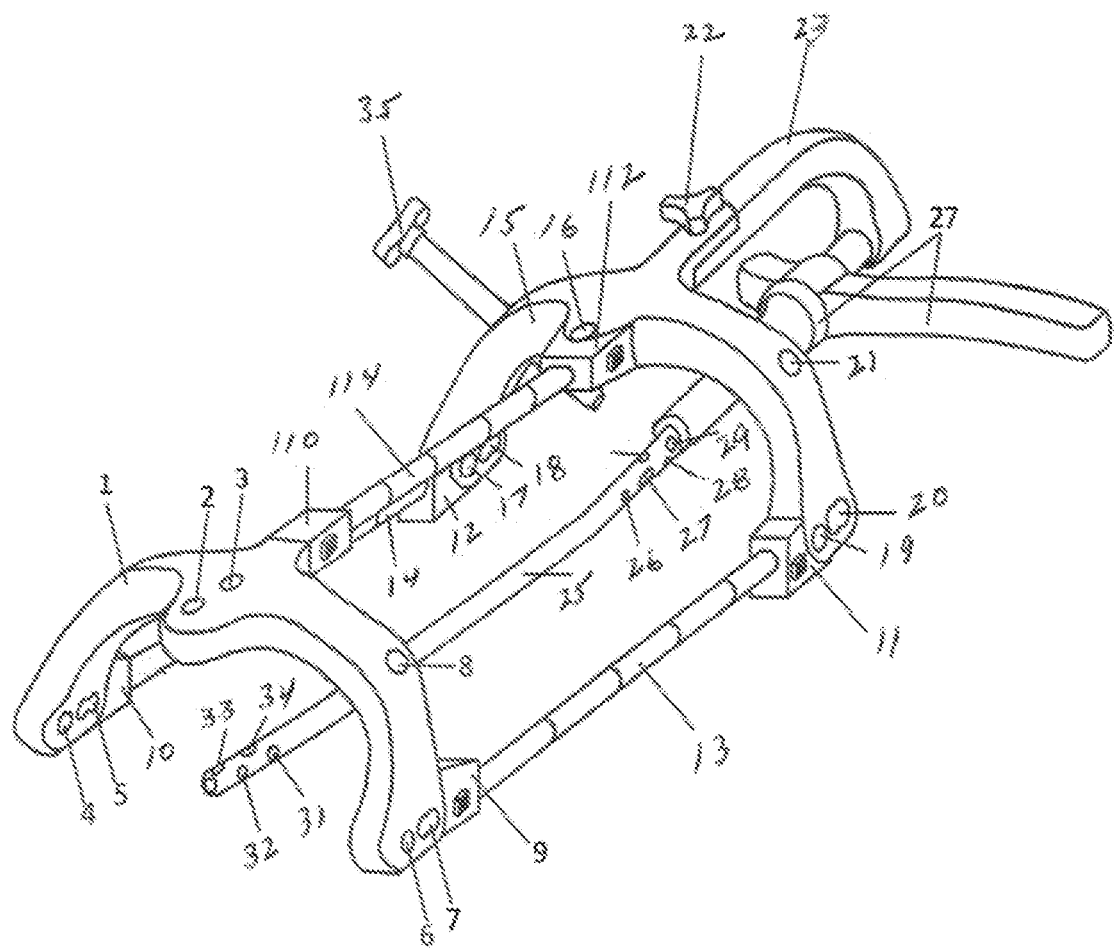
FIG. 5 is a perspective view of the IM tibial nail aiming guide according to some embodiments of the present invention, e.g., having corresponding third distal and proximal aiming guide angle modulators with associated third locking mechanisms and a corresponding third support bar.

FIG. 5 shows an IM tibial nail aiming guide according to an alternative embodiment of the present invention, e.g., having corresponding third distal and proximal aiming guide angle modulators with associated third locking mechanisms (110 and 112) coupled to a corresponding third support bar (114). In FIG. 5, all the elements of the IM tibial nail aiming guide shown in FIGS. 1-4B are shown and identified with corresponding reference numerals. The alternative embodiment of the IM tibial nail aiming guide disclosed herein is consistent with that disclosed in the aforementioned provisional application, although some reference nos. have been suitable adapted and modified to improve the overall readability of the present application in relation to FIGS. 1-5 of the drawing as a whole.

In particular, in the IM tibial nail aiming guide shown in FIG. 5, the distal aiming guide (1) is configured with a third distal aiming guide angle modulator with a third locking mechanism (110); the proximal aiming guide (15) is also configured with a third proximal aiming guide angle modulator with a third locking mechanism (112); and a third support bar (114) is configured to couple third locking mechanisms (110 and 112) together in a manner similar to the way the two support bars (13-14) respectively couple together the locking mechanisms (9, 11; 10, 12).

Similar to the support bars (13-14), the third support bar (114) is configured with corresponding telescopic abilities with associated telescopic extenders (38) and locking mechanism (39) that rigidly fixes the third support bar (114) at the desired length, e.g., consistent with that shown and described in relation to FIG. 3A herein.

Similar to the associated locking mechanisms (9, 11; 10, 12), each locking mechanism (110, 112) may be configured with a corresponding hinge joint having a corresponding angle modulator, angle locking device and angled measuring dial guide, which allow for corresponding accurate angling and rigid fixation of the proximal and distal aiming guides (1,15) independent to each other to accommodate any tibial IM nail's proximal and distal bends, e.g., consistent with that shown and described in relation to FIGS. 4A and 4B herein.

REFERENCES

1. Levin, P. E., Schoen, R. W., Jr, & Browner, B. D. (1987). Radiation exposure to the surgeon during closed interlocking intramedullary nailing. *The Journal of bone and joint surgery. American volume,* 69(5), 761-766.
2. Moreschini, O., Petrucci, V., & Cannata, R. (2014). Insertion of distal locking screws of tibial intramedullary nails: A comparison between the free-hand technique and the SURESHOT® Distal Targeting System. *Injury,* 45(2), 405-407. See https://doi:10.1016/j.injury.2013.09.023
3. Allard, A., Letissier, H., Le Nen, D., Dubrana, F., & Di Francia, R. (2021). Evaluation of the accuracy of the Sureshot® electromagnetic targeting system in distal locking of long-nailed humeral diaphyseal fractures. *Orthopaedics & traumatology, surgery & research: OTSR,* 107(2), 102785. See https://doi.org/10.1016/j.otsr.2020.10278
4. Veen, E. J., Ettema, H. B., Zuurmond, R. G., & Mostert, A. K. (2011). Are there any advantages in using a distal aiming device for tibial nailing? Comparing the Centro Nailing System with the Unreamed Tibia Nail. *Injury,* 42(10), 1049-1052. See https://doi.org/10.1016/j.injury.2011.03.056
5. Gugala Z, Nana A, Lindsey R W. Tibial intramedullary nail distal interlocking screw placement: comparison of the free-hand versus distally-based targeting device techniques. Injury 2001; 32(Suppl. 4 SD):21-5.

What I claim is:

1. An intramedullary (IM) tibial nail aiming guide for coupling to an IM tibial nail having proximal and distal holes for receiving proximal and distal screws, the IM tibial nail aiming guide comprising:
    an IM tibial nail proximal insertion handle configured to insert the IM tibial nail into a medulla of a patient's tibia;
    a proximal aiming guide having proximal guide holes passing through for drilling and receiving the proximal screws for coupling to the proximal holes in the IM tibial nail, and having an IM tibial nail coupling portion configured to couple to the IM tibial nail proximal insertion handle when the IM tibial nail aiming guide is connected to the IM tibial nail;
    proximal hinge joints configured to couple to the proximal aiming guide and angle and lock the proximal aiming guide in relation to the IM tibial nail to be inserted into the medulla of the patient's tibia;
    a distal aiming guide having distal guide holes for drilling and receiving the distal screws for coupling to the distal holes in the IM tibial nail; and
    distal hinge joints configured to couple to the distal aiming guide and angle and lock the distal aiming guide in relation to the IM tibial nail to be inserted into the medulla of the patient's tibia; and
    telescopic support bars configured to couple the proximal hinge joints to the distal hinge joints and to expand or contract and lock in order to change a length between the proximal aiming guide and the distal aiming guide to accommodate different IM tibial nails having different tibial nail lengths.

2. The IM tibial nail aiming guide according to claim 1, wherein the proximal aiming guide has a C-shape and the proximal guide holes include an AP proximal guide hole, two transverse proximal guide holes, and two oblique proximal guide holes.

3. The IM tibial nail aiming guide according to claim 1, wherein the distal aiming guide has a C-shape and the distal guide holes include two AP distal guide holes, two transverse distal guide holes, and two oblique distal guide holes.

4. The IM tibial nail aiming guide according to claim 1, wherein each proximal hinge joint includes an angle modulator, an angle locking device, and an angled measuring dial guide.

5. The IM tibial nail aiming guide according to claim 1, wherein each distal hinge joint includes an angle modulator, an angle locking device, and an angled measuring dial guide.

6. The IM tibial nail aiming guide according to claim 1, wherein each telescopic support bar includes at least one telescopic extender configured to change a length of the respective telescopic support bar and a locking mechanism configured to rigidly fix the length of the respective telescopic support bar.

7. The IM tibial nail aiming guide according to claim 1, wherein the IM tibial nail aiming guide is made in whole or in part of a radiolucent material.

8. The IM tibial nail aiming guide according to claim 1, wherein
    the proximal hinge joints include two or three proximal hinge joints;
    the distal hinge joints include two or three distal hinge joints; and
    the telescopic support bars include two or three telescopic support bars, each telescopic support bar configured to couple a respective proximal hinge joint to a respective distal hinge joint.

9. The IM tibial nail aiming guide according to claim 1, wherein the IM tibial nail coupling portion includes location pins to be inserted through location pin holes on the IM tibial nail proximal insertion handle when the IM tibial nail aiming guide is connected to the IM tibial nail.

10. The IM tibial nail aiming guide according to claim 9, wherein the IM tibial nail aiming guide includes a locking mechanism comprising a thumb screw configured to securely tighten the IM tibial nail coupling portion to the IM tibial nail proximal insertion handle creating a complete rigid structure.

11. A method for coupling an intramedullary (IM) tibial nail aiming guide to an IM tibial nail having proximal and distal holes for receiving proximal and distal screws, the method comprising:
    configuring an IM tibial nail proximal insertion handle to insert the IM tibial nail into a medulla of a patient's tibia;
    configuring a proximal aiming guide with proximal guide holes passing through for drilling and receiving the proximal screws for coupling to the proximal holes in the IM tibial nail, and with an IM tibial nail coupling portion configured to couple to the IM tibial nail proximal insertion handle when the IM tibial nail aiming guide is connected to the IM tibial nail;
    coupling proximal hinge joints to the proximal aiming guide to angle and lock the proximal aiming guide in relation to the IM tibial nail to be inserted into the medulla of the patient's tibia;

configuring a distal aiming guide with distal guide holes for drilling and receiving the distal screws for coupling to the distal holes in the IM tibial nail;

coupling distal hinge joints to the distal aiming guide to angle and lock the distal aiming guide in relation to the IM tibial nail to be inserted into the medulla of the patient's tibia; and coupling telescopic support bars to the proximal hinge joints and the distal hinge joints to expand or contract and lock in order to change a length between the proximal aiming guide and the distal aiming guide to accommodate different IM tibial nails having different tibial nail lengths.

12. The method according to claim 11, wherein the method comprises configuring the proximal aiming guide with a C-shape, wherein the proximal guide holes include an AP proximal guide hole, two transverse proximal guide holes, and two oblique proximal guide holes.

13. The method according to claim 11, wherein the method comprises configuring the distal aiming guide with a C-shape, wherein the distal guide holes include two AP distal guide holes, two transverse distal guide holes, and two oblique distal guide holes.

14. The method according to claim 11, wherein the method comprises configuring each proximal hinge joint with an angle modulator, an angle locking device, and an angled measuring dial guide.

15. The method according to claim 11, wherein the method comprises configuring each distal hinge joint with an angle modulator, an angle locking device, and an angled measuring dial guide.

16. The method according to claim 11, wherein the method comprises configuring each telescopic support bar with at least one telescopic extender to change a length of the respective telescopic support bar and with a locking mechanism to rigidly fix the length of the respective telescopic support bar.

17. The method according to claim 11, wherein the method comprises configuring the IM tibial nail aiming guide in whole or in part from a radiolucent material.

18. The method according to claim 11, wherein the method comprises
configuring the proximal hinge joints as two or three proximal hinge joints;
configuring the distal hinge joints as two or three distal hinge joints; and
configuring the telescopic support bars as two or three telescopic support bars, and coupling each telescopic support bar to a respective proximal hinge joint and a respective distal hinge joint.

19. The method according to claim 11, wherein the method comprises configuring the IM tibial nail coupling portion with location pins to be inserted through location pin holes on the IM tibial nail proximal insertion handle when the IM tibial nail aiming guide is connected to the IM tibial nail.

20. The method according to claim 19, wherein the method comprises configuring the IM tibial nail aiming guide with a locking mechanism comprising a thumb screw to securely tighten the IM tibial nail coupling portion to the IM tibial nail proximal insertion handle creating a complete rigid structure.

* * * * *

UNITED STATES PATENT AND TRADEMARK OFFICE
CERTIFICATE OF CORRECTION

| | |
|---|---|
| PATENT NO. | : 11,806,061 B2 |
| APPLICATION NO. | : 17/980832 |
| DATED | : November 7, 2023 |
| INVENTOR(S) | : Jordan Andre Bauer |

It is certified that error appears in the above-identified patent and that said Letters Patent is hereby corrected as shown below:

On the Title Page

Item (54) and in the Specification, Column 1, Lines 1-3 should read:
"DESIGN AND METHOD FOR PROXIMAL AND DISTAL SCREW FIXATION IN INTRAMEDULLARY TIBIAL NAILS".

Signed and Sealed this
Twelfth Day of December, 2023

Katherine Kelly Vidal
*Director of the United States Patent and Trademark Office*